United States Patent [19]

Kulsa et al.

[11] 4,080,340
[45] Mar. 21, 1978

[54] NITROIMIDAZOLES

[75] Inventors: Peter Kulsa, Scotch Plains, N.J.; Clarence S. Rooney, Worcester, Pa.

[73] Assignee: Merck & Co., Inc., Rahway, N.J.

[21] Appl. No.: 723,414

[22] Filed: Sep. 15, 1976

Related U.S. Application Data

[60] Division of Ser. No. 600,252, Jul. 30, 1975, Pat. No. 4,010,176, which is a division of Ser. No. 301,420, Oct. 27, 1972, Pat. No. 3,915,978, which is a continuation of Ser. No. 1,307, Jan. 7, 1970, Pat. No. 3,711,495.

[51] Int. Cl.$^2$ .............................................. C07D 413/14
[52] U.S. Cl. ............................ 260/307 F; 260/307 H; 424/272
[58] Field of Search ....................... 260/307 H, 307 F

[56] References Cited

U.S. PATENT DOCUMENTS

| 3,711,495 | 1/1973 | Kulsa et al. ........................... 260/309 |
| 3,915,978 | 10/1975 | Kulsa et al. ....................... 260/307 F |
| 4,010,176 | 3/1977 | Kulsa et al. ....................... 260/307 H |

Primary Examiner—Richard J. Gallagher
Assistant Examiner—Jose Tovar
Attorney, Agent, or Firm—Walter Patton; Hesna J. Pfeiffer

[57] ABSTRACT

Novel substituted nitroimidazoles are provided, for example, 2-(4,5-substituted-isoxazol-3-yl)-1-substituted-5-nitroimidazole; 2-(4,5-disubstituted-$\Delta^2$-isoxazolin-3-yl)-1-substituted-5-nitroimidazole; or 2-(4,5-disubstituted-2-loweralkyl-isoxazolidin-3-yl)-1-substituted-5-nitroimidazole. These compounds have antibacterial and antiprotozoal activity especially against human and animal trypanosomiasis and trichomoniasis.

2 Claims, No Drawings

NITROIMIDAZOLES

This is a divisional application of copending application U.S. Ser. No. 600,252, filed July 30, 1975, and issued to U.S. Pat. No. 4,010,176 which is a divisional application of copending U.S. Ser. No. 301,420, filed Oct. 27, 1972 and issued to U.S. Pat. No. 3,915,978 which is a continuation of copending application U.S. Ser. No. 1,307, filed Jan. 7, 1970 and issued to U.S. Pat. No. 3,711,495.

This invention relates to isoxazol-3-yl-, $\Delta^2$-isoxazolin-3-yl-, or isoxazolidin-3-yl-substituted-5-nitroimidazoles.

These compounds have the following respective structures:

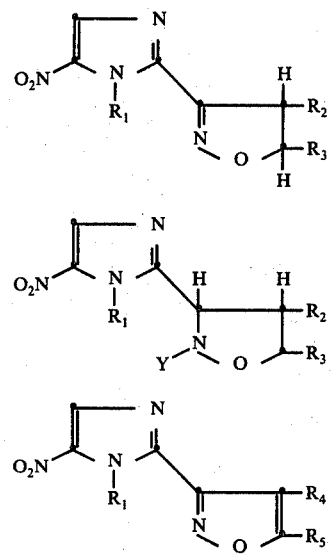

wherein $R_1$ is hydrogen, loweralkyl having 1–6 carbon atoms, or —CH$_2$CH$_2$OH, Y is loweralkyl having 1–6 carbon atoms, benzyl, or hydrogen, $R_2$ and $R_3$ are the same or different and are each hydrogen, loweralkyl having 1–6 carbon atoms, alkoxycarbonyl, carboxamido, N-alkylcarboxamide, N,N-dialkylcarboxamide, amino, phenyl, alkylamino, dialkylamino, or $R_2$ and $R_3$ are a ring structure having the following structure:

—CH$_2$—$_n$, n equals an integer 3–10;

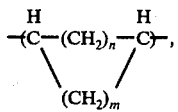

m equals an integer from 1–3;
n equals an integer from 1–2;
—CH$_2$-SO$_2$-CH$_2$—
—(CH$_2$)$_m$—O—, m equals an integer from 2–3;

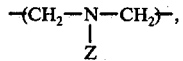

Z equals hydrogen or benzoyl;

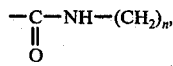

n equals an integer from 1–4,

and $R_4$ and $R_5$ are the same or different and are each hydrogen, loweralkyl having 1–6 carbon atoms, alkoxycarbonyl, carboxamido, N-alkylcarboxamide, N,N-dialkylcarboxamide amino, phenyl, alkylamino, or dialkylamino; or $R_4$ and $R_5$ are a ring structure of —CH$_2$—$_n$, n equals an integer from 3–10; except that when only one of $R_2$ and $R_3$ or $R_4$ and $R_5$ are hydrogen, the substituent other than hydrogen is on the 5-position of the ring. Whenever the term "alkyl" is used throughout the specification, a lower alkyl group having 1–6 carbon atoms is intended.

The novel compounds disclosed in this invention are prepared following three different processes. The isoxazolyl derivatives are prepared by reacting an acetylene derivative with a 1-loweralkyl-5-nitroimidazol-2-hydroxamoyl chloride.

The $\Delta^2$-isoxazolinyl derivatives are prepared by reacting an olefin with a 1-loweralkyl-5-nitroimidazol-2-hydroxamoyl chloride.

The isoxazolidinyl derivatives are prepared by reacting an olefin with an α-(1-methyl-5-nitroimidazol-2-yl)-N-alkylnitrone. These processes are separately discussed in greater detail hereinafter.

The reactive olefin used to prepare both the $\Delta^2$-isoxazolinyl and the isoxazolidinyl derivatives can be defined as

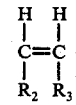

wherein $R_2$ and $R_3$ are the same or different and are each hydrogen, loweralkyl having 1–6 carbon atoms, alkoxycarbonyl, carboxamido, N-alkylcarboxamide, N,N-dialkylcarboxamide phenyl, or $R_2$ and $R_3$ are a ring structure having the following structure:

—CH$_2$—$_n$, n equals an integar from 3–10;

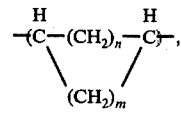

m equals an integer from 1–3;
n equals an interger from 1–2;
—CH$_2$-SO$_2$-CH$_2$—
—(CH$_2$)$_m$—O—,
m equals an integer from 1–3;

Z equals hydrogen or benzoyl;

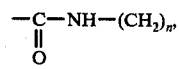

n equals an integer from 1–4;

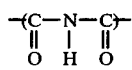

The acetylene compound used to prepare the isoxazolyl derivative can be defined as

wherein $R_4$ and $R_5$ are the same or different and are each hydrogen, loweralkyl having 1–6 carbon atoms, alkoxycarbonyl, carboxamido, N-alkylcarboxamide, N,N-dialkylcarboxamide, or phenyl.

The above acetylene compound is reacted with the chosen 1-loweralkyl-5-nitroimidazol-2-hydroxamoyl chloride of the following structure:

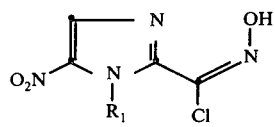

wherein $R_1$ is hydrogen, loweralkyl having 1–6 carbon atoms, or $CH_2CH_2OH$, to prepare the isoxazolyl derivative. The hydroxamoyl chloride is prepared from the 2-formyl-1-substituted-5-nitroimidazole following procedures known in the art. For example, reaction with hydroxylamine is followed by chlorination with nitrosyl chloride. Preparation of the 2-formyl starting material is described in Belgium Pat. No. 661,262 issued Sept. 17, 1965.

The acetylene and the hydroxamoyl chloride are reacted in an inert solvent such as tetrahydrofuran, benzene, or chloroform. The molar ratio of the hydroxamoyl chloride to the acetylene is approximately 1:1, although 1:1–15 can be used. The reaction takes place in the presence of an organic base, such as an alkylamine, for example, triethylamine, N-methyl piperidine, or any suitable tertiary amine. The temperature of the reaction is preferably 0°–25° C. Lower temperatures may be used, to −20° C., and the operable upper temperature limit is such that substantially no acetylene polymerization occurs. The reaction takes place in form ½ to 10 hours.

It is noted that neither the reactive olefin nor the reactive acetylene contain the substituents amino, alkylamino, or dialkylamino, although this moiety can be present on the final nitroimidazole. The process of preparing these functions utilizes first an olefin or an acetylene containing either alkorycarbonyl or a carboxamido group at any one of positions $R_2$, $R_3$, $R_4$, or $R_5$. The reaction with the desired nitroimidazole is completed as described above; the final isoxazolyl-, $\Delta^2$-isoxazolinyl-, or isoxazolidinyl-nitroimidazole is prepared. This nitroimidazole is then hydrolyzed in acidic or basic aqueous solution to remove either the alkoxycarbonyl group or the carboxamido group, thereby producing the free carboxylic acid functionality at positions $R_2$, $R_3$, $R_4$, or $R_5$ of the corresponding ring. Following hydrolysis, the acid chloride is prepared by reacting with thionyl chloride or oxalyl chloride. The acid chloride is then reacted with an alkali metal azide, such as sodium, potassium, or lithium azide to prepare the acid azide of the nitroimidazole. This latter acid azide can be rearranged to the corresponding isocyanate by heating to reflux in an inert organic solvent such as benzene, xylene, or the like. The isocyanate can be treated with mineral acid such as HCL $H_2SO_4$ or the like to prepare the free amino substituent. Alternately, the isocyanate can be reacted at elevated temperatures with methanol in an inert organic solvent as above to prepare thiocarbamate, and the latter removed by acid or base hydrolysis to yield the final amine.

After the amine is obtained on the ring, the nitroimidazole can be treated with a loweralkyl halide, loweralkyl having 1–6 carbon atoms, for instance, methyl iodide, ethyl chloride, n-butyl iodide, hexyl bromide, or the like. An inert organic solvent such as ethanol, methanol, dimethyl formamide, and an elevated temperature between 60°–120° C. can be used. The amino group at $R_2$, $R_3$, $R_4$, or $R_5$ is then alkylated within 1–2 hours. If a molecular equivalent is used, the secondary amine is produced, or an alkylamino group at $R_2$, $R_3$, $R_4$, or $R_5$. If an excess of reagent is used, the tertiary amine, the dialkylamino group, is produced at $R_2$, $R_3$, $R_4$, or $R_5$. If an unsymetrical tertiary amine is desired, the reaction can be conducted in two stages, with a molecular equivalent of each desired alkyl halide being used in each step.

The above described acetylene can only be used to prepare an isoxazolyl derivative in which $R_4$ and $R_5$ are not joined in a ring structure. When an isoxazolyl derivative is desired which has a cyclic substituent on positions 4 and 5 of the isoxazole ring, a morpholino-substituted olefin having the following formula:

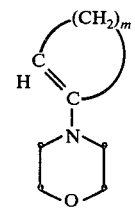

wherein $n$ is an integer from 3 to 10, can be reacted with the hydroxamoyl chloride in the presence of an organic base, such as triethylamine. An inert solvent system is used, for instance, tetrahydrofuran is suitable. The reaction takes place in from ½ to 2 hours at 0°–25° C. The compound thus prepared is a morpholine-substituted $\Delta^2$-isoxazoline having the following formula:

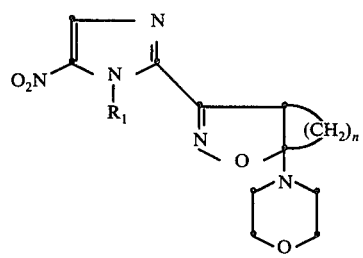

This latter compound can be isolated, and treated with a strong mineral acid to remove the element or morpholine thereby preparing the desired compound:

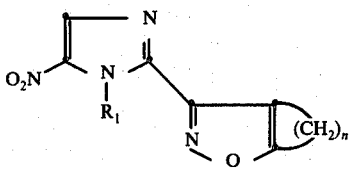

The Δ²-isoxazolinyl derivatives are also prepared from the 1-loweralkyl-5-nitroimidazol-2-hydroxamoyl chloride by reaction of the latter with the olefin defined above. There are two different sets of process conditions. In one route, the olefin and the hydroxamoyl chloride are reacted in an inert solvent at reflux. The solvent is chosen so that the reflux temperature is preferably 100°–150° C., and can be 80°–200° C. The ratio of hydroxamoyl chloride to olefin is approximately 1:1, although 1:1–15 can be used. The reaction takes place in about 18 to 24 hours.

The other route used to prepare the Δ²-isoxazolinyl derivative utilizes the presence of an organic base, such as alkylamine, for example, triethylamine, N-methyl piperidine or any other suitable tertiary amine. The reaction takes place in a solvent such as tetrahydrofuran at low temperatures, preferably from 0°–25° C. The reaction takes place in from ½ to 10 hours.

The isoxazolindinyl derivatives are prepared by reacting an olefin as described above with an α-(1R₁-5-nitroimidazol-2-yl)-N-alkylnitrone of the following formula:

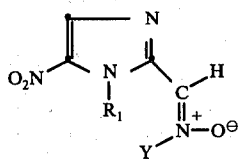

III wherein $R_1$ is hydrogen, loweralkyl having 1–6 carbon atoms, or $CH_2CH_2OH$, and Y is H, loweralkyl or benzyl. This nitrone can be prepared from a 2-formyl-1-substituted-5-nitroimidazole by reaction with a benzyl- or alkyl-substituted-hydroxylamine, such as

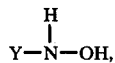

wherein Y is hydrogen, a benzyl radical or an alkyl radical having 1–6 carbon atoms. The hydroxylamine can preferably be employed in the salt form, such as the hydrochloride, acetate carbonate and others, or in the free base form. The two reactants are mixed together and allowed to react at room temperature to 60° C. for 2–12 hours in a solvent such as methanol, ethanol, or water. The desired product can be isolated after the solution is made alkaline with an inorganic base.

The chosen nitrone is then reacted with an olefin chosen from the group described above. The reactants are reacted in an inert solvent at reflux, and operably at a temperature of about 80°–200° C., and preferably 100°–150° C. The ratio of nitrone to olefin is approximately 1:1, althrough 1:1–15 can be used. The reaction takes place in about 1–12 hours.

The novel compounds of this invention have antibacterial and antiprotozoal activity especially against human and animal trypanosomiasis, including Chages' disease, and trichomoniasis.

Trypanosomiasis is a term used to describe a group of allied protozoal diseases, each of which is due to infection with a species of the genus Trypanosoma. They reach their greatest importance in Africa where their presence in enzootic form precludes the keeping of domestic animals throughout the largest part of the continent between 15° N and 20° S latitude. The pathogenic trypanosomes of Africa are considered to be primarily associated with the tsetse flies (glossira) which feed on vertebrate blood. Wherever tsetse are present, trypanosomiasis will also be found in some part of the mammalian population. The clinical findings are typically those of a wasting disease with intermittent fever. Anemia, edema, and cachexia are parts of the syndrome.

The important trypanosomes pathogenic to domestic animals are *T. congolense, T. simiae, T. vivax,* and *T. brucci.* The latter trypanosome is morphologically identical to *T. gambiense,* responsible for human "sleeping sickness" of Africa. A trypanosome found in the Western Hemisphere is *T. cruzi,* which affects both domestic animals and man.

Acute Chages' disease (*T. cruzi*) occurs predominantly in young children. The chronic form may be mild and asymptomatic, but complications from myocarditis and C.N.S. involvement may result with fatal outcome.

Trichomoniasis is a protozoan disease affecting cattle, poultry, and humans. In cattle the causative protozoan is *Trichomonas foetus* which produces a contagious venereal disease characterized by sterility, pyometra and abortion. *Trichomonas gallinarum* invades the lower intestine of domestic birds and causes diarrhea and lesions in the intestinal wall. In humans the infective protozoa are *Trichomonas vaginalis, infecting the vagina and prostate, and Trichomonas hominis,* found in the intestine.

The compounds of this invention have particular value in the control of trypanosomiasis and trichomoniasis in domesticated animals, particularly cattle. For this purpose, they may be administered orally with an ingestible carrier as a component of the animal feedstuff, in the drinking water, in salt blocks and in unit dosage forms such as boluses and drenches. The amount of active ingredient required for optimum control of trypanosomiasis varies in accordance with such factors as the particular compound employed, the species of animal to be treated, the species of infecting parasite, the severity of infection, and whether the compound is employed therapeutically or prophylactically. In general, the compounds defined by Formula I, when administered orally to domestic animals in daily doses of from about 0.1 mg. to about 500 mg. per kilogram of animal body weight are highly effective in controlling trypanosomiasis and trichomoniasis without intolerable toxic effect. When these compounds are to be employed as therapeutic agents, good results are obtained when the animals are fed a daily dose of from about 5 mg. to about 500 mg. and preferably 15 mg. to 250 mg. per kilogram of body weight.

Administration may be in a single dose or divided into a plurality of smaller doses over a period of 24 hours. Where prophylactic treatment is desired and the compounds are fed continuously, satisfactory results are obtained when the animals ingest daily dosages of about 0.1 mg. to 100 mg. per kilogram of body weight. The unit dosage forms may be readily prepared by conventional formulating techniques and are particularly useful when administration is to be made in a single dose or divided doses over a period of 24 hours.

The exact amount of active ingredient to be employed in the above compositions may vary provided that a sufficient amount is ingested to give the required dosage. In general, tablets, boluses and drenches containing from about 5% to 70% by weight of active ingredient may be satisfactorily employed to supply the desired dosage.

The substituted imidazoles defined by Formula I above may be administered, dispersed in or admixed with the normal elements of animal sustenance, i.e., the feed, drinking water or other liquids normally partaken by the animals. This method is preferred when it is desired to administer the active compounds continuously, either as a therapeutic or prophylactic agent, for a period of several days or more. However, in such usage, it is to be understood that the present invention also contemplates the employment of compositions containing the active compounds intimately dispersed in or admixed with any other carrier or diluent which is inert with respect to the active ingredient, orally administrable and is tolerated by the animals.

When the compounds described according to Formula I above are provided as a constituent of the feed, the required dosage may be supplied with feed compositions containing from about 0.001% to 3% by weight of the active compound. Such medicated feed compositions can be prepared for direct use by mixing the above amount of active ingredient directly with the feed. The medicated feeds may also be prepared by the use of feed supplements containing a higher concentration of the active ingredient uniformly dispersed in a solid edible carrier such as corn meal, wheat shorts, alfalfa, etc. In general, feed supplements containing from about 5% to about 50% by weight of active ingredient may be satisfactorily employed to supply the desired dosage in the finished feed.

In the preparation of feed supplements, the active ingredient is added to the carrier and the whole mixed to give substantially uniform dispersion of the antitrypanosomiasis agent in the carrier.

When the substituted nitroimidazoles of this invention are used in the prevention and treatment of Chagas' disease and human "sleeping sickness", the compounds can be administered as intravenous, intramuscular, or interperitoneal injections. The compounds are suspended or dissolved in an inert non-toxic pharmaceutically acceptable carrier and administered. When used as a prophylactic, 2-12 mg./kg. of body weight are injected every 1-8 months. The compounds can also be used orally against Chagas' disease or human "sleeping sickness". The oral dosage is 3-20 mg. per kg. twice a day for 5-10 days. This therapy can be given alone or in addition to other drugs useful against trypanosomiasis, such as sodium suramin, melarsoprol, tryparsamide, or pentamidine.

The compounds of the present invention are also useful as topical trichomonacides. When employing the compounds in this manner, one or more of the active agents are uniformly distributed in a suitable chemotherapeutic vehicle that is chemically compatible with the particular compound selected, non-inhibiting with respect to the action of the effective agent upon the parasite and essentially non-injurious to body tissue under the conditions of use. The vehicle is preferably a semi-liquid or semi-solid type and the final preparation may be in the form of a suppository if desired.

Oil and water types of emulsions or creams as well as aqueous jellies such as those prepared with the aid of any of a number of commercially used jelling agents including acacia, tragacanth, bentonite, alginic acid and the like are suitable vehicles. The vehicle may also be a viscous aqueous gel containing one or more cellulose derivatives such as methyl cellulose, hydroxyethyl cellulose, and sodium carboxymethyl cellulose. Gelling agents such as pectin, gum tragacanth, sodium alginate and other vegetable gelling agents are also useful vehicles in this regard.

This invention is more fully described in a reading of the following examples. The first four examples show the preparation of the 5-nitroimidazole starting materials. These preparations are exemplary only to show one of several possible methods of preparing these compounds.

EXAMPLE 1

1-Methyl-5-nitroimidazole 24.2 G., (0.214 moles) of 4(5)-nitroimidazole is heated with 24.0 g. (0.11 mole) of methyl tosylate for one hour at 180°–190° C. and cooled to give a hard solid. The mixture is shaken with 175 ml. of 2.5 N aqueous sodium hydroxide until it is dissolved and diluted with 175 ml. of water to give an oily precipitate. The mixture is extracted with ether; the ether extract washed with 2.5 N aqueous hydrochloric acid and water. The aqueous acid wash is treated with excess aqueous sodium hydroxide and extracted with ether. This latter ether extract is evaporated to dryness and recrystallized from petroleum ether to yield 1-methyl-5-nitroimidazole, m.p. 154°–155° C.

In accordance with the above procedure but starting with ethyl tosylate, propyl tosylate, or n-butyl tosylate in place of methyl tosylate, there is obtained 1-ethyl-5-nitroimidazole, 1-propyl-5-nitroimidazole, and 1-n-butyl-5-nitroimidazole.

EXAMPLE 2

1-Methyl-2-hydroxymethyl-5-nitroimidazole 27.9 g. of 1-methyl-5-nitroimidazole prepared as in Example 1 and 30.1 g. of paraformaldehyde are added to 154 ml. of dimethylsulfoxide and the resulting solution is sealed into a glass-lined tube. The solution is heated at 110° C. for 24 hours, with shaking. The dimethylsulfoxide is removed by distillation at 53°–56° C./2 mm. The residue is extracted with 3 × 150 ml. of hot benzene. The benzene extracts are combined and cooled to room temperature. 1-Methyl-2-hydroxymethyl-5-nitroimidazole crystallizes, and is recovered by filtration. The yield of product is 23 g., m.p. 112°–114.5° C.

When 1-ethyl-5-nitroimidazole, 1-propyl-5-nitroimidazole, 1-n-butyl-5-nitroimidazole, and 4(5)-nitroimidazole are used in the above reaction, respectively, the following compounds are prepared: 1-ethyl-2-hydroxymethyl-5-nitroimidazole; 1-propyl-2-hydroxymethyl-5-nitroimidazole; 1-n-butyl-2-hydroxymethyl-5-nitroimidazole; and 2-hydroxymethyl-5-nitroimidazole.

EXAMPLE 3

1-Methyl-2-formyl-5-nitroimidazole 100 g. (0.64 mole) of 1-methyl-2-hydroxymethyl-5-nitroimidazole prepared as in Example 2 is dissolved in 3500 ml. of benzene at 70° C. There is added over a 20 minute period 460 g. of lead tetraacetate (previously washed with glacial acetic acid and air dried in the dark). The reaction mixture is stirred at 78° C. for 8 hours during which time white, crystalline lead diacetate precipitates from the solution. The mixture is allowed to stand overnight at room temperature, and the lead diacetate then removed by filtration and washed with 2 × 100 ml. of benzene. The combined benzene filtrate and washes ae extracted with 1500 ml. of water and then with two 1 liter portions of saturated aqueous potassium bicarbonate.

The dried extracts are evaporated in vacuo to give a residue of substantially pure 1-methyl-2-formyl-5-nitroimidazole. Recrystallization of the product from 500 ml. of boiling hexane affords 79 g. of 1-methyl-2-formyl-5-nitroimidazole, m.p. 90°–94° C.

When this general procedure is followed using 1-ethyl-2-hydroxymethyl-5-nitroimidazole, 1-propyl-2-hydroxymethyl-5-nitroimidazole, 1-n-butyl-2-hydroxymethyl-5-nitroimidazole, and 2-hydroxymethyl-5-nitroimidazole, the following compounds are respectively prepared: 1-ethyl-2-formyl-5-nitroimidazole; -1-propyl-2-formyl-5-nitroimidazole; 1-n-butyl-2-formyl-5-nitroimidazole; and 2-formyl-5-nitroimidazole.

EXAMPLE 4

1-(2'-Acetoxyethyl)-5-nitroimidazole 4.0 g. of 4(5)-nitroimidazole and 4.7 ml. of β-ethoxyethyl tosylate are heated together in a 170°–175° C. oil bath for one hour with occasional stirring until the mixture becomes homogeneous. The mixture is cooled to near room temperature and dissolved by agitating with a mixture of about 50 ml. of chloroform and 50 ml. 4N ammonium hydroxide. The chloroform phase is extracted twice with 2N ammonium hydroxide and dried over sodium sulfate. Evaporation to dryness in vacuo gives a black syrup which is filtered through 30 g. of basic alumina eluting with 1,2-dichloroethane, ether. The very pale yellow band which comes through the column fairly rapidly is collected and evaporated in vacuo to give a yellow oil which crystallizes on seeding. The crude product is recrystallized from ether-hexane giving pale brown crystals of 1-(2'-ethoxyethyl)-5-nitroimidazole.

57 mg. of the above product is heated at 100° C. in 0.3 ml. concentrated sulfuric acid for one-half hour. The mixture is diluted with 1.5 ml. water and heated an additional hour. The solution is treated with charcoal, diluted with 1 ml. water and treated dropwise with 0.7 ml. of 11.7 N sodium hydroxide while cooled in ice. The crystalline precipitate which forms is filtered off, washed with water and air dried. This material is recrystallized from benzene and then with charcoal treatment from methanol-water giving 1-(2'-hydroxyethyl)-5-nitroimidazole, m.p. 101°–102° C.

Acetylation of 15 g. of the latter product with 10 g. of acetic anhydride in 30 ml. of pyridine at reflux for 20 minutes yields 1-(2'-acetoxyethyl)-5-nitroimidazole, m.p. 61°–62° C.

EXAMPLE 5

1-(2'-Acetoxyethyl)-2-formyl-5-nitroimidazole

A mixture of 24.25 g. of 1-(2'-acetoxyethyl)-5-nitroimidazole prepared as in Example 4, 15 g. of paraformaldehyde and 150 ml. of dimethylsulfoxide is heated in a sealed tube overnight at 100°–150° C. The dimethylsulfoxide is removed completely at reduced pressure, and the residue is dissolved in water and extracted with chloroform. The chloroform extract is dried and concentrated. The residue is dissolved in ethyl acetate, and the solution is charged on a column of alumina. Elution with ethyl acetate and evaporation of the solvent yields 1-(2'-acetoxyethyl)-2-hydroxymethyl-5-nitroimidazole, m.p. 138°–145° C.

This compound is then treated following the procedure of Example 1 with lead tetraacetate. After purification, 3-(2'-acetoxyethyl)-2-formyl-5-nitroimidazole is identified.

This latter compound can be used in any of the following Examples which use the starting 2-formyl-1-substituted-5-nitroimidazoles of Example 3. After using this compound to form the desired cyclic-substituted nitroimidazole, the acetate can be removed using hydrolysis to yield the desired 1-(2'-hydroxyethyl)-2-substituted-5-nitroimidazole.

The following Example, Example 6, shows the preparation of the nitrone of Formula III. Example 7 is the preparation of the hydroxyamoyl chloride of Formula II.

EXAMPLE 6

α-(1-Methyl-5-nitroimidazol-2-yl)-N-methylnitrone

To a solution of 1-methyl-2-formyl-5-nitroimidazole prepared as in Example 3, (4.65 g., 0.03 mole) in 75 ml. of methanol is added 2.5 g. (0.03 mole) of N-methylhydroxylamine hydrochloride $CH_3NHOH.HCl$. The mixture is allowed to stand at room temperature for 4 hours. A precipitate forms which is recovered and dissolved in 40 ml. of water. Solid sodium bicarbonate is added until the solution has a basic pH and a precipitate desposits again. After filtration and recrystallization from methanol, 1.8 g. of the product α-(1-methyl-5-nitroimidazol-2-yl)-N-methylnitrone is recovered having a melting point of 180° C. (with decomposition).

The corresponding α-(1-ethyl-5-nitroimidazol-2-yl)-N-methylnitrone, α-(1-propyl-5-nitroimidazol-2-yl)-N-methylnitrone, and α-[1-(2'-acetoxyethyl)-5-nitroimidazol-2-yl]-N-methylnitrone can be prepared in a similar fashion utilizing the respectively 1-substituted-2-formyl-5-nitroimidazoles disclosed in Examples 3 and 5.

The corresponding α-(1-methyl-5-nitroimidazol-2-yl)-N-benzylnitrone can also be prepared using N-benzylhydroxylamine hydrochloride in the above reaction with 1-methyl-2-formyl-5-nitroimidazole.

EXAMPLE 7

1-Methyl-5-nitroimidazole-2-hydroxamoylchloride 15.5 g. of 1-methyl-2-formyl-5-nitroimidazole prepared as in Example 3is dissolved in 300 ml. of ethanol and heated to 80° C. The mixture is added to a hot solution of 7.65 g. of $NH_2OH.HCl$ in 30 ml. of water. The mixture is refrigerated overnight. Filtration and crystallization yielded a yellow crystalline material, having a melting point of 251°–252° C. (dec.). This intermediate oxime product is dissolved in 50 ml. of dimethylformamide at 0° C. A solution of NOCl (13.1 g. in 200 ml. of dimethylformamide) is added dropwise with stirring. The mixture is stirred at 0° C. for 15 minutes and 45 minutes at room temperature. It is quenched by pouring into 2500 ml. of cold water, and the precipitate filtered, washed and dried. A sample is recrystalized from ethyl acetate and dried under vacuum. The product obtained has a melting point of 185°–186° C. and is identified as 1-methyl-5-nitroimidazole-2-hydroxamoylchloride. The corresponding 1-(2'-acetoxyethyl)-5-nitroimidazole-2-hydroxamoylchloride, 1-ethyl-5-nitroimidazole-2-hydroxamoylchloride, 1-n-butyl-5-nitroimidazole-2-hydroxamoylchloride, and 5-nitroimidazole-2-hydroxamoylchloride are prepared respectively from 1-(2'-acetoxyethyl)-2-formyl-5-nitroimidazole, 1-ethyl-2-formyl-5-nitroimidazole, 1-n-butyl-2-formyl-5-nitroimidazole, and 2-formyl-5-nitroimidazole prepared as in Examples 3 and 5.

The following Examples 8 to 35 all have the structural formula given. However, only the oxygen-containing ring is drawn. When the "NI" is used, it is meant to be the corresponding 1-methyl-5-nitroimidazol-2-yl ring.

EXAMPLE 8

1-Methyl-2-(2-methyl-5-carbomethoxy-isoxazolindin-3-yl)-5-nitroimidazole

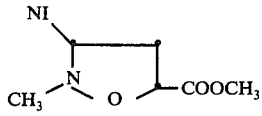

The compound prepared in Example 6, α-(1-methyl-5-nitroimidazol-2-yl)-N-methylnitrone (4.0 g.) is added to 50 ml. of methylacrylate and is refluxed at about 80° C. for one hour. At the end of this time, excess methylacrylate is removed under vacuum. The residue is purified by recrystallization from methanol. The product recovered is identified as 1-methyl-2-(2-methyl-5-carbomethoxy-isoxazolindin-3-yl)-5-nitroimidazole having a melting point of 105°–106° C. The corresponding benzyl derivative, 1-methyl-2-(2-benzyl-5-carbomethoxy-isoxazolindin-3-yl)-5-nitroimidazole is prepared using a α-(1-methyl-5-nitroimidazol-2-yl)-N-benzylnitrone.

EXAMPLE 9

1-Methyl-2-(2-methyl-4,5-hexamethylene-isoxazolindin-3-yl)-5-nitroimidazole hydrochloride

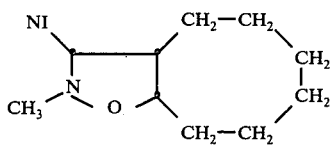

1.87 g. of the compound prepared in Example 6, α-(1-methyl-5-nitroimidazol-2-yl)-N-methylnitrone, and 1.1 g. of cyclooctene are added in 30 ml. of toluene. The mixture is refluxed for about 16 hours. At the end of this period, the nitrone is dissolved. The reaction mixture, after filtering, is evaporated to a yellow oil. This oil is purified by chromatographic techniques on silica gel with a benzene:chloroform eluent. 2.5 g. of a clear yellow oil is obtained. This oil is then mixed with ether containing dry hydrochloric acid to obtain 2.4 g. of a crystalline material. After recrystallization from 2-propanol, a solid is obtained having a melting point of 193° C. with decomposition. This solid is identified as 1-methyl-2-(2-methyl-4,5-hexamethylene-isoxazolindin-3-yl)-5-nitroimidazole hydrochloride. The analogous compound prepared using α-(1-methyl-5-nitroimidazol-2-yl)-N-benzylnitrone is identified as 1-methyl-2-(2-benzyl-4,5-hexamethylene-isoxazolindin-3-yl)-5nitroimidazole hydrochloride.

EXAMPLE 10

1-Methyl-2-(2-methyl-5-carbamoyl-isoxazolindin-3-yl)-5-nitroimidazole

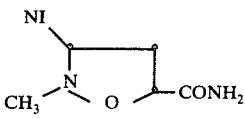

5.52 g. of the nitrone prepared in Example 6 is refluxed with 2.34 g. of acrylamide in 100 ml. of tetrahydrofuran. After 3 hours, an additional 1.0 g. of acrylamide in 40 ml. of tetrahydrofuran is added and refluxing continued. After 12 hours, the reaction mixture is cooled and filtered. After purification, 3.4 g. of the product, 1-methyl-(2-methyl-5-carbamoyl-isoxazolindin-3-yl)-5-nitroimidazole, having a melting point of 214°–215° C. (dec.) is recovered. The corresponding 1-methyl-2-(2-benzyl-5-carbamoyl-isoxazolindin-3-yl)-5-nitroimidazole is prepared using the N-benzylnitrone described in Example 6.

The product 1-methyl-2-(2-methyl-5-carbamoyl-isoxazolindin-3-yl)-5-nitroimidazole is then heated in an acidic solution to recover the hydrolysis product, 1-methyl-2-(2-methyl-5-carboxylic acid-isoxazolindin-3-yl)-5-nitroimidazole. This latter product, after treating following the procedure of Example 14, yields 1-methyl-2-(2-methyl-5-amino-isoxazolindin-3-yl)-5-nitroimidazole.

EXAMPLE 11

1-Methyl-2-[2-methyl-5-(N-methyl)-carbamoyl-isoxazolindin-3-yl]-5-nitroimidazole

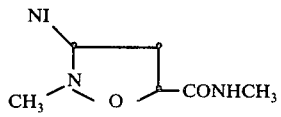

5.4 g. of the nitrone prepared in Example 6 is refluxed with 2.5 g. of N-methylacrylamide in 100 ml. of tetrahydrofuran. After 2 hours, an additional 1.0 g. of N-methylacrylamide in 40 ml. of tetrahydrofuran is added and refluxing continued. After 8 hours, the reaction mixture is cooled and filtered. After purification, the product, 1-methyl-2-[2-methyl-5-(N-methyl)-carbamoyl-isoxazolindin-3-yl]-5-nitroimidazole, is recovered.

In an analogous manner, using N-benzylnitrone and N-ethylacrylamide; or N-benzylnitrone and N-hexylacrylamide, the corresponding products, 1-methyl-2-[2-benzyl-5-(N-ethyl)-carbamoyl-isoxazolindin-3-yl]-5-nitroimidazole and 1-methyl-2-[2-benzyl-5-(N-hexyl)-carbamoyl-isoxazolindin-3-yl]-5-nitroimidazole are prepared.

Also, when N,N-dimethylacrylamide or N-methyl-N-propylacrylamide are employed in the above reaction with the nitrone as prepared in Example 6, the products 1-methyl-2-[2-methyl-5-(N,N-dimethyl)-carbamoyl-isoxazolindin-3-yl]-5-nitroimidazole and 1-methyl-2-[2-methyl-5-(N-methyl-N-propyl)-carbamoyl-isoxazolindin-3-yl]-5-nitroimidazole are formed.

EXAMPLE 12

1-Methyl-2-(5-carboethoxyisoxazol-3-yl)-5-nitroimidazole

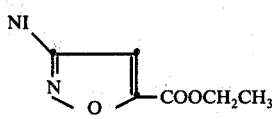

8.2 g. of the hydroxamoylchloride prepared in Example 7 are dissolved in 160 ml. of tetrahydrofuran at 0° C. To the solution is added a cold solution of triethylamine tetrahydrofuran (0.04 mole in 40 ml.). After one minute, a solution of ethylpropiolate (5.0 g.) in 10 ml. of tetrahydrofuran is added. The reaction mixture is stirred at 0° C. for one-half hour and then at room temperature for one hour. The mixture is then filtered and the filtrate is reduced under vacuum leaving an orange crystalline mass. After recrystallization from ethanol, the product is obtained which has a melting point of 114°–115° C. This product is identified as 1-methyl-2-(5-carboethoxyisoxazol-3-yl)-5-nitroimidazole.

EXAMPLE 13

1-Methyl-2-(5-carbamoyl-isoxazol-3-yl)-5-nitroimidazole.

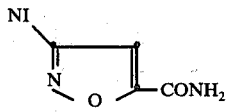

3 g. of the compound prepared in Example 12 is dissolved in hot methanol. The solution is saturated with ammonia. A precipitate is formed and the mixture is cooled by placing in the refrigerator. After filtration and purification, the pure product having a melting point of 235°–238° C. is recovered. This product is identified as 1-methyl-2-(5-carbamoyl-isoxazol-3-yl)-5-nitroimidazole.

EXAMPLE 14

1-Methyl-2-(5-aminoisoxazol-3-yl)-5-nitroimidazole

1-Methyl-2-(5-methylaminoisoxazol-3-yl)-5-nitroimidazole

1-Methyl-2-(5-aminomethylhexylisoxazol-3-yl)-5-nitroimidazole 4 g. of the compound prepared in Example 13, 1-methyl-2-(5-carbamoylisoxazol-2-yl)-5-nitroimidazole, are dissolved in 30 ml. of a 10% HCl solution, and the mixture heated to reflux. After 30 minutes, the reaction is terminated and the product, 1-methyl-2-(5-carboxylic acid-isoxazol-3-yl)-5-nitroimidazole, is obtained.

1.5 g. of the acid prepared above are refluxed in oxalyl chloride (25 ml.) until a clear solution is obtained, after about 6 hours. Excess reagent is removed under vacuum. The product, 1-methyl-2-(5-carboxylic acid chloride-isoxazol-8-yl)-5-nitroimidazole is dissolved in 50 ml. acetone. A solution of sodium azide (0.4 g. of NaN$_3$) in 5 ml. of water is added all at once. After stirring for 15 minutes, an additional 100 ml. of water is added and stirring continued for another 15 minutes. The product is 1-methyl-2-(5-carboxylic acid azideisoxazol-3-yl)-5-nitroimidazole. 1.4 g. of the latter is dissolved in 60 ml. of benzene and refluxed for 3 hours. 10 ml. of concentrated HCl are then added and refluxing continued for ½ hour. The reaction is diluted with chloroform and made basic. The dried organic phase yielded 0.5 g. of the product, 1-methyl-2-(5-aminoisoxazol-3-yl)-5-nitroimidazole, m.p. 180°–185° C.

0.25 g. of 1-methyl-2-(5-aminoisoxazol-3-yl)-5-nitroimidazole, prepared above, are dissolved in 20 ml. of dimethylformamide. 0.16 g. of methyl iodide are added, and the reaction mixture is heated to 80° for one hour. The solvent and unreacted reagents are removed, and the product recrystallized. The product is 1-methyl-2-(5-methylamino-isoxazol-3-yl)-5-nitroimidazole.

The product prepared above is treated in a similar fashion with hexyl chloride in dimethylformamide for two hours. The recrystallized product is identified as 1-methyl-2-(5-methylhexylaminohexylisoxazol-3-yl)-5-nitroimidazole.

EXAMPLE 15

1-Methyl-2-(4,5,6,7-tetrahydrobenz[d]isoxazol-3-yl)-5-nitroimidazole

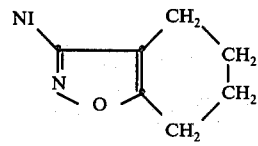

To a suspension of 2.04 g. of the hydroxamoyl chloride prepared in Example 7 in 30 ml. of tetrahydrofuran at 0° C. is added a solution of triethylamine and 1-morpholino-3,4,5,6-tetrahydrobenzene (1.01 g. of triethylamine and 1.67 g. of the morpholino compound). The mixture is stirred 15 minutes at 0° C. and one-half hour at room temperature. The tetrahydrofuran is evaporated. The residue is dissolved in dichloromethane and is washed with sodium bicarbonate solution. The organic phase is dried and evaporated to a yellow oil. After treatment with diethyl ether, a crystalline product is obtained. A sample recrystallized from methanol has a melting point of 153°–156° C. This product is an intermediate in the synthesis and is a $\Delta^2$-isoxazoline compound with a morpholino substituent. It is identified as 1-methyl-2-(4,5-tetramethylene-5-morpholino-$\Delta^2$-isoxazolindin-3-yl)-5-nitroimidazole, m.p. 155° C.

This latter morpholine compound (10 g.) is dissolved in concentrated sulfuric acid (100 ml.) and heated on a steam bath for one and one-half hours. The yellow reaction mixture is poured onto ice to quench. After filtration, a crude product is obtained. It is recrystallized from methanol and yields 4.5 g. of a product identified as 1-methyl-2-(4,5,6,7-tetrahydrobenz[d]isoxazol-3-yl)-5-nitroimidazole, having a melting point of 161°–162° C.

The following Examples 16 through 36 relate to the preparation of the $\Delta^2$-isoxazoline. It will be clear to one skilled in the art that, although the 1-methyl derivatives are prepared, the other loweralkyl, acetoxyethyl, and unsubstituted derivatives can be prepared from the corresponding hydroxamoyl chloride compounds in Example 7.

EXAMPLE 16

1-Methyl-2-(5-carbomethoxy-Δ²-isoxazolin-3-yl)-5-nitroimidazole

To a solution of the hydroxamoyl chloride compounds prepared in Example 7 in tetrahydrofuran (4.02 g. in 80 ml.) at 0° C. is added with stirring 2.7 ml. of methylacrylate. Following this addition, a solution of triethylamine in tetrahydrofuran (2.02 g. in 20 ml.) is added dropwise to the solution. The mixture is stirred 10 minutes at 0° C. then one hour at room temperature. The triethylamino hydrochloride is filtered and then tetrahydrofuran is removed under vacuum. The residue is taken up in chloroform and washed with a dilute solution of sodium bicarbonate. After drying, the organic layer is evaporated and the residual yellow oil is crystallized. The product is identified as 1-methyl-2-(5-carbomethoxy Δ²-isoxazolin-3-yl)-5-nitroimidazole, and has a melting point of 109°–110° C.

EXAMPLE 17

1-Methyl-2-(5-carbamoyl-Δ²-isoxazolin-3-yl)-5-nitroimidazole

The compound prepared in Example 16 is dissolved in methanol (119 mg. in 10 ml.). Ammonia is bubbled through the solution until a precipitate formed. The mixture is filtered after one hour and purification and recrystallization yield 95 mg. of the product, 1-methyl-2-(5-carbamoyl-Δ³-isoxazolin-3-yl)-5-nitroimidazole, having a melting point of 238°–239° C. This latter compound can be treated following the procedure of Example 14 to yield 2-(5-amino-Δ²-isoxazolin-3-yl)-5-nitroimidazole.

EXAMPLE 18

1-Methyl-2-(5-phenyl-Δ²-isoxazolin-3-yl)-5-nitroimidazole 2.04 g. of the hydroxamoylchloride prepared in Example 7 are dissolved in 40 ml. of tetrahydrofuran. One gram of styrene is added and the solution is kept at 0° C. while a solution of triethylamine tetrahydrofuran (1.01 g. in 10 ml.) is added. The mixture is stirred 15 minutes at 0° C. and one hour at room temperature. After filtering and removing the excess solvent, the residue is taken up in chloroform and washed with a dilute solution of sodium bicarbonate. Evaporation of the dried extract yields a yellow oil which recrystallizes from methanol as a pale yellow crystalline material. This material has a melting point of 133°–134° C. and is identified as 1-methyl-2-(5-phenyl-Δ²-isoxazolin-3-yl)-5-nitroimidazole.

EXAMPLE 19

1-Methyl-2-(4,5-cyclodimethylsulfone-Δ²-isoxazolin-3-yl)-5-nitroimidazole 0.408 g. of the hydroxamoylchloride prepared in Example 7 are dissolved in 8 ml. of tetrahydrofuran containing 0.5 g. of dihydrothiophene-1,1-dioxide at 0° C. To this solution is added dropwise with stirring a 0.202 g. solution of triethylamine in 2 ml. of tetrahydrofuran. The mixture is stirred for 15 minutes at 0° C. and one hour at room temperature. After filtering and removing the solvent, the residue is treated with chloroform and washed with sodium bicarbonate solution. The dried organic layer after purification and recrystallization yields a product identified as 1-methyl-2-(4,5-cyclodimethylsulfone-Δ²-isoxazolin-3-yl)-5-nitroimidazole, having a melting point of 208°–209° C.

EXAMPLE 20

1-Methyl-2-(3a,5,6,7a-tetrahydro-4H-pyrano[3,2-d]-isoxazol-3-yl)-5-nitroimidazole Following the same general procedure of Examples 16 through 19, the hydroxamoylchloride prepared as in Example 7 is reacted with dihydropyran at 0° C. The product, after recrystallization, is identified as 1-methyl-2-(3a, 5,6,7a-tetrahydro-4H-pyrano[3,2-d]-isoxazol-3-yl)-5-nitroimidazole, having a melting point of 140°–142° C.

EXAMPLE 21

1-Methyl-2-(3a,4,5,6a-tetrahydro-4,6-dioxo-4H-pyrrolo[3,4-d]-Δ²-isoxazol-3-yl)-5-nitroimidazole Following the same general procedure of Examples 16 through 19, the hydroxamoylchloride prepared as in Example 7 is reacted with maleimide. The product, after recrystallization, is identified as 1-methyl-2-(3a,4,6,6a-tetrahydro-4,6-dioxo-4H-pyrrolo[3,4-d]-Δ²-isoxazol-3-yl)-5-nitroimidazole, having a melting point of 259° C. (dec.).

EXAMPLE 22

1-Methyl-2-(5-hexyl-Δ²-isoxazolin-3-yl)-5-nitroimidazole.

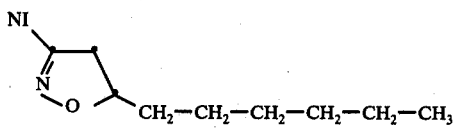

Following the same generel procedure of Examples 16 through 19, the hydroxamolychloride prepared as in Example 7 is reacted with octene-1. The product, after recrystallization, is identified as 1-methyl-2-(5-hexyl-Δ²-isoxazolin-3-yl)-5-nitroimidazole, having a melting point of 50°–51° C.

EXAMPLE 23

1-Methyl-2-(Δ²-isoxazolin-3-yl)-5-nitroimidazole

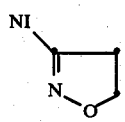

Following the same general proceduce of Examples 16 through 19, the hydroxamoylchloride prepared as in Example 7 is reacted with ethylene. The product, after recrystallization, is identified as 1-methyl-2-(Δ²-isoxazolin-3-yl)-5-nitroimidazole, having a melting point of 103°–105° C.

EXAMPLE 24

1-Methyl-2-(4,5-cis-dimethyl-Δ²-isoxazolin-3-yl)-5-nitroimidazole

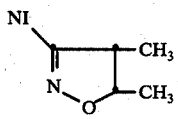

Following the same general procedure of Examples 16 through 19 the hydroxamoylchloride prepared as in Example 7 is reacted with cis-2-butene. The product, after recrystallization, is identified as 1-methyl-(4,5-cis-dimethyl-Δ²-isoxazolin-3-yl)-5-nitroimidazole, having a melting point of 83°–84° C.

EXAMPLE 25

1-Methyl-2-(4,5-trans-dimethyl-Δ²-isoxazolin-3-yl)-5-nitroimidazole

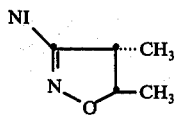

Following the same general procedure of Examples 16 through 19, the hydroxamoylchloride prepared as in Example 7 is reacted with trans-2-butene. The product, after recrystallization, is identified as 1-methyl-2-(4,5-trans-dimethyl-Δ²-isoxazolin-3-yl)-5-nitroimidazole, having a melting point of 65°–67° C.

EXAMPLE 26

Exo-2-(3a,4,5,6,7,7a-hexahydro-4,7-methano-1,2-benzisoxazol-3-yl)-1-methyl-5-nitroimidazole

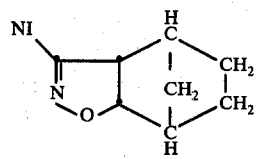

Following the same general procedure of Examples 16 through 19, the hydroxamoylchloride prepared as in Example 7 is reacted with norbornene. The product, after recrystallization, is identified as exo-2-(3a,4,5,6,7,-7a-hexahydro-4,7-methano-1,2-benz-isoxazol-3-yl)-1-methyl-5-nitroimidazole, having a melting point of 124°–125° C.

EXAMPLE 27

1-Methyl-2-(5-benzoyl-3a,5,6,6a-tetrahydro-4H-pyrrolo[3,4-d]-isoxazol-3-yl)-5-nitroimidazole

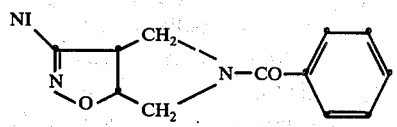

Following the same general procedure of Examples 16 through 19, the hydroxamoylchloride prepared as in Example 7 is reacted with N-benzoyl-2,5-dihydropyrolle. The product, after recrystallization, is identified as 1-methyl-2-(5-benzoyl-3a,5,6,6a-tetrahydro-4H-pyrrolo[3,4-d]-isoxazol-3-yl)-5-nitroimidazole, having a melting point of 153°–155° C.

EXAMPLE 28 trans-1-Methyl-2-[3a,4,5,6,7,8,9,9a-octahydrocyclooct[d]-isoxazol-3-yl)-5-nitroimidazole

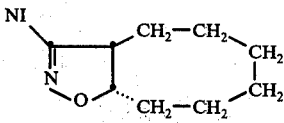

Following the same general procedure of Examples 16 through 19, the hydroxamoylchloride prepared as in Example 7 is reacted with trans-cyclooctene. The product, after recrystallization, is identified as trans-1-methyl-2-[3a,4,5,6,7,8,9,9a-octahydrocyclooct[d]-isoxazol-3-yl]-5-nitroimidazole, having a melting point of 106°–109° C.

EXAMPLE 29

1-Methyl-2-(3a,5,6,6a-tetrahydro-4H-cyclopent[d]-isoxazol-3-yl)-5-nitroimidazole

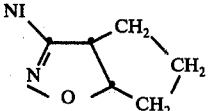

Following the same general procedure of Examples 16 through 19, the hydroxamoylchloride prepared as in Example 7 is reacted with cyclopentene. The product, after recrystallization, is identified as 1-methyl-2-(3a,5,6,6a-tetrahydro-4H-cyclopent[d]-isoxazol-3-yl)-5-nitroimidazole, having a melting point of 89.5°–91.5° C.

EXAMPLE 30

1-Methyl-2-(3a,4,5,6,7,8,9,9a-octahydrocyclooct[d]-isoxazol-3-yl)-5-nitroimidazole

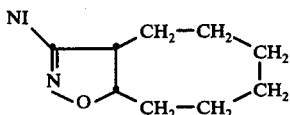

408 mg. of the hydroxamoylchloride prepared in Example 7 and 224 mg. of cyclooctene are added to 6 ml. of toluene and refluxed for 14 hours. The mixture is cooled and passed through a thin-layer chromatographic column of 10 g. of silica gel, using benzene as an eluent. The fractions containing the product are reduced to yield a yellow crystalline material. This product is recrystallized from hexane, yielding the product, 1-methyl-2-(3a,4,5,6,7,8,9,9a-octahydrocyclooct[d]-isoxazol-3-yl)-5-nitroimidazole, having a melting point of 113.5 to 115° C.

EXAMPLE 31

1-Methyl-2-(3a,4,5,6,7,7a-hexahydro-1,2-benz-isoxazol-3-yl)-5-nitroimidazole

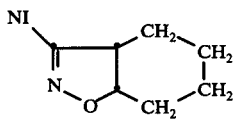

Following the same procedure as in Example 30, the hydroxamoylchloride prepared as in Example 7 is reacted with cyclohexene. The product, 1-methyl-2-(3a,4,5,6,7,7a-hexahydro-1,2-benz-isoxazol-3-yl)-5-nitroimidazole has a melting point of 120°–121° C.

EXAMPLE 32

1-Methyl-cis-2-(3a,5,6,7,8,8a-hexahydro-4H-cyclohept[d]-isoxazol-3-yl)-5-nitroimidazole

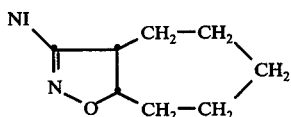

Following the same procedure as in Example 30, the hydroxamoylchloride prepared as in Example 7 is reacted with cycloheptene. The product, 1-methyl-cis-2-(3a,5,6,7,8,8a-hexahydro-4H-cyclohept[d]-isoxazol-3-yl)-5-nitroimidazole, having a melting point of 93°–95° C.

EXAMPLE 33

1-Methyl-trans-2-(3a,4,5,6,7,8,9,10,11,12,13,13a-dodecahydrocyclododec[d]-isoxazol-3-yl)-5-nitroimidazole

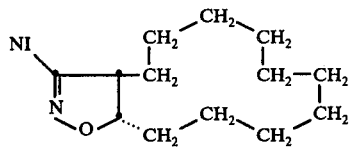

Following the same procedure as in Example 30, the hydroxamoylchloride prepared as in Example 7 is reacted with cyclododecene. The product, 1-methyl-trans-2-(3a,4,5,6,7,8,9,10,11,12,13,13a-dodecahydrocyclododec[d]-isoxazol-3-yl)-5-nitroimidazole, having a melting point of 121°–122° C.

EXAMPLE 34

1-Methyl-2-(trans-4,5-dipropyl-$\Delta^2$-isoxazolin-3-yl)-5-nitroimidazole

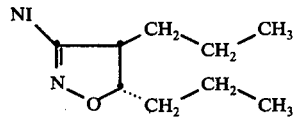

6.12 g. of the hydroxamoylchloride prepared as in Example 7 is refluxed with 3.4 g. of trans-4-octene for 18 hours. The reaction mixture is then worked up following a similar procedure as in Example 30, The product obtained, 1-methyl-2-(trans-4,5-dipropyl-$\Delta^2$-isoxazolin-3-yl)-5-nitroimidazole, has a melting point of 34°–36° C.

EXAMPLE 35

1-Methyl-2-(trans-4,5-diethyl-$\Delta^2$-isoxazolin-3-yl)-5-nitroimidazole

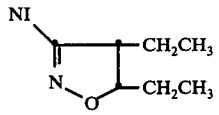

Following the same procedure as in Example 34, the hydroxamoylchloride is reacted with trans-3-hexene. The product, 1-methyl-2-(trans-4,5-diethyl-$\Delta^2$-isoxazolin-3-yl)-5-nitroimidazole, has a melting point of 66°–67° C.

EXAMPLE 36

1-Methyl-2-(4,5-hexano-C-lactam-$\Delta^2$-isoxazolin-3-yl)-5-nitroimidazole

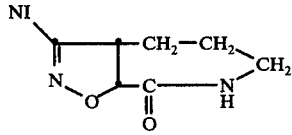

Following the same procedure as in Example 33, the hydroxamoylchloride is reacted with 6-amino-2-hexenoic acid lactam:

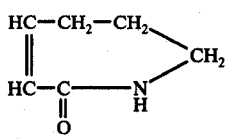

The product, 1-methyl-2-(4,5-hexano-ε-lactam-Δ²-isoxazolin-3-yl)-5-nitroimidazole is recovered.

We claim:

1. A 1,2-disubstituted-5-nitroimidazole having the following structure:

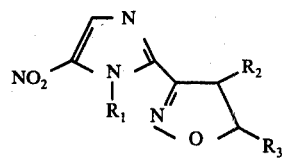

wherein $R_1$ is hydrogen, loweralkyl having 1 to 6 carbon atoms or $-CH_2-CH_2-OH$ and $R_2$ and $R_3$ together represent a ring structure having the following structure:

$-(CH_2)_m-O-$, where $m$ equals an integer of from 2 to 3.

2. The compound of claim 1 which is 1-methyl-2-(3a,5,6,7a-tetrahydro-4H-pyrano[3,2-d]-isoxazol-3-yl)-5-nitroimidazole.

* * * * *